United States Patent
Axelson, Jr. et al.

(10) Patent No.: US 10,182,828 B2
(45) Date of Patent: Jan. 22, 2019

(54) RESECTION GUIDE AND METHOD OF POSITIONING

(71) Applicant: Stryker Corporation, Kalamazoo, MI (US)

(72) Inventors: Stuart L. Axelson, Jr., Succasunna, NJ (US); Michael A. McGovern, Wyckoff, NJ (US); Rahul Ramachandran, Madison, NJ (US)

(73) Assignee: Stryker Corporation, Kalamazoo, MI (US)

( * ) Notice: Subject to any disclaimer, the term of this patent is extended or adjusted under 35 U.S.C. 154(b) by 1439 days.

(21) Appl. No.: 14/075,437

(22) Filed: Nov. 8, 2013

(65) Prior Publication Data
US 2015/0133943 A1 May 14, 2015

(51) Int. Cl.
*A61B 17/17* (2006.01)
*A61B 17/15* (2006.01)

(52) U.S. Cl.
CPC .................................. *A61B 17/155* (2013.01)

(58) Field of Classification Search
CPC ...... A61B 17/15; A61B 17/154; A61B 17/155
See application file for complete search history.

(56) References Cited

U.S. PATENT DOCUMENTS

| | | | |
|---|---|---|---|
| 6,962,593 B2 | 11/2005 | Sanford et al. | |
| 7,060,074 B2 | 6/2006 | Rosa et al. | |
| 7,601,154 B2 | 10/2009 | Kuczynski et al. | |
| 7,608,079 B1 | 10/2009 | Blackwell et al. | |
| 8,740,911 B2 | 6/2014 | Librot et al. | |
| 8,828,016 B2 | 9/2014 | Major et al. | |
| 9,089,342 B2 * | 7/2015 | Carroll | A61B 17/155 |
| 2004/0153087 A1 | 8/2004 | Sanford et al. | |
| 2005/0192588 A1 * | 9/2005 | Garcia | A61B 17/155 606/88 |
| 2006/0241634 A1 | 10/2006 | Tuttle et al. | |
| 2009/0216285 A1 | 8/2009 | Ek et al. | |

OTHER PUBLICATIONS

Triathlon PKR, "Partial knee resurfacing surgical protocol", Copyright 2011.

* cited by examiner

*Primary Examiner* — Anu Ramana
(74) *Attorney, Agent, or Firm* — Lerner, David, Littenberg, Krumholz & Mentlik, LLP

(57) ABSTRACT

A bone resection guide, which includes a profiling guide. The profiling guide includes a first planar bone contact surface, a first guide surface and at least one outline corresponding to at least a portion of a first implant.

9 Claims, 17 Drawing Sheets

RESECTION GUIDE AND METHOD OF POSITIONING

BACKGROUND OF THE INVENTION

The knee joint includes three bones, namely the femur, tibia and patella. The distal end of the femur lies adjacent to the proximal end of the tibia while the patella lies adjacent the anterior portion of the femur. The joint elements that engage one another are preferably covered by articular cartilage. Specifically, the distal end of the femur and the proximal end of the tibia are covered by articular cartilage, as is the posterior surface of the patella.

The articular cartilage of the knee joint may become damaged due to degeneration and/or wear, which may lead to bone-to-bone contact during articulation of the joint. This may result in significant pain and potential damage to the bone surfaces. A knee replacement procedure may be required in cases where damage to the articular cartilage is significant. Depending on the extent of the damage, the procedure may include at least partial replacement of one or more bones of the knee joint. For instance, in a total knee replacement each of the bones of the knee joint is at least partially covered by implants. In other instances, a knee arthroplasty procedure may be limited to portions of one of the joints. For instance, a patellofemoral procedure is limited to at least partial replacement of the engagement surfaces between the femur and the patella.

The distal femur includes medial and lateral compartments which make up the tibiofemoral joint ("TFJ") and the patellofemoral compartment which makes up the patellofemoral joint ("PFJ"). The PFJ more specifically includes the patella and the trochlear groove of the femur, and the TFJ includes the lateral and medial condyles of the femur and the tibial plateau.

A number of diseases and injuries may affect the articular cartilage within any or all of these compartments. Some of these conditions may include osteoarthritis, rheumatoid arthritis, genetic defects and/or traumatic injuries. These conditions can lead to severe pain and functional limitations that may reduce a sufferer's quality of life.

Where the damage affects the PFJ and either the lateral or medial compartments of the TFJ, a total knee arthroplasty ("TKA") or a bicompartmental knee arthroplasty ("BKA") may be indicated. A TKA typically removes bone within all three compartments and seeks to replace the articular surfaces of these compartments with a series of implants. A TKA may be an option of last resort in that it often results in the removal of at least one or both of the cruciate ligaments, which may reduce proprioception and natural, functional performance. Additionally, TKA is near the end of the spectrum of joint replacement options. Thus, a TKA may eliminate the flexibility of taking a gradual approach of replacing bone as the need arises.

In contrast, a BKA may leave the cruciate ligaments and the lateral or medial condyle intact with the option of receiving a TKA in the future if warranted. BKA's that resurface the PFJ and one compartment of the TFJ often resurface each compartment separately. Thus, the surgeon may perform a patellofemoral arthroplasty followed by a unicondylar arthroplasty. An example of a patellofemoral arthroplasty can be found disclosed in U.S. Provisional Application No. 61/768,765 and an example of a unicondylar arthroplasty can be found in U.S. Pat. No. 8,377,069, the disclosures of which are hereby incorporated by reference herein in their entirety.

Given the close proximity of the TFJ and PFJ compartments, impingement of the resected surfaces that receive the prostheses is cause for concern as it may interfere with a precise fit and functioning of the implants. Current resection guide instrumentation may make it difficult for the surgeon to visualize the size and spread of a unicondylar implant prior to making a distal femoral resection, which may inhibit precise sizing and locational placement of the implant. Further, this instrumentation makes it difficult to visualize the location of the resections for the unicondylar implant with respect to resections for a patellofemoral implant prior to making the required distal cut, which may increase the risk of impingement.

BRIEF SUMMARY OF THE INVENTION

According to a first aspect of the present disclosure, a bone resection guide which includes a profiling guide. The profiling guide includes a first planar bone contact surface, a first guide surface and a first outline corresponding to at least a portion of a first implant.

Additionally, the first outline may be at least a portion of the perimeter of the profiling guide and may correspond to at least a portion of the perimeter of the first implant. Further, the first outline may correspond to an anterior portion of the first implant.

Continuing with this aspect, the profiling guide may include a second outline corresponding to a second implant. The first and second implants may be different sizes. The profiling guide may also include a third outline corresponding to a third implant. The third implant may be a different size from the first and second implants. Additionally, the first, second and third outlines may correspond to anterior portions of the first, second and third implants, respectively, and the first, second and third implants may be femoral condylar implants. In another example of the first aspect, the profiling guide may include a plurality of outlines each corresponding to one of a plurality of implants, wherein each of the plurality of implants is of a different size.

In another aspect of the present disclosure, a profiling guide which includes a first bone contact surface. The first bone contact surface defines a first plane for contacting a first portion of a femoral condyle. The profiling guide also includes a periphery that defines at least a portion of an outer perimeter of the first bone contact surface. The at least a portion of the outer perimeter of the first bone contact surface is dimensioned to substantially correspond to at least a portion of a periphery of a first condylar implant.

The bone resection guide may also include a posterior referencing guide. The posterior referencing guide may include a second bone contact surface, which may define a second plane for contacting a second portion of the femoral condyle. The posterior referencing guide may be coupled to the profiling guide such that the first plane intersects the second plane. In one example, the first plane may orthogonally intersect the second plane at a vertex away from the femoral condyle when the first and second bone contact surfaces contact the first and second portions of the femoral condyle, respectively.

Additionally, the profiling guide may include a first resection aperture that extends through the first bone contact surface orthogonally with respect to the first bone contact surface. The profiling guide may also include a second resection aperture extending through the first bone contact surface at an oblique angle with respect to the first bone contact surface.

Continuing with this aspect, the bone resection guide may also include a distal resection guide. The distal resection guide may include a resection slot. The distal resection guide may be adapted to be coupled to an extension of the profiling guide such that the resection slot is orthogonal to the first resection aperture.

In a further aspect of the present disclosure, a method of resecting a femur bone to receive a condylar implant. The method includes the step of placing an inner surface of a profiling guide against an unresected distal portion of the femur bone. The profiling guide includes a periphery dimensioned to substantially correspond to at least a portion of a periphery of a condylar implant. The method also includes the step of adjusting the periphery of the profiling guide such that the periphery does not intersect an anteriorly resected surface of the femur bone.

Additionally, the method may include the step of coupling a distal resection guide that includes a resection slot to the profiling guide. The resection slot may be parallel to the first bone contact surface of a profiling guide, and may have an axis transverse to the anterior resected surface. The method may further include the steps of coupling a posterior referencing guide to the profiling guide, and contacting a posterior portion of the femur bone with an inner surface of the posterior referencing guide.

Continuing with this aspect, the method may include the step of resecting a portion of the femur bone through the resection slot of the distal resection guide along a second distal plane parallel and offset from a first distal plane of the profiling guide to form a planar distal surface of the femur bone. Further the method may include the step of placing the inner surface of the profiling guide against the planar distal surface. Additionally, the method may further include the step of resecting a portion of the femur bone through the resection slot of the distal resection guide to define a second resected area such that a first resected area defined by the anterior resected surface does not intersect the second resected area.

In an additional aspect of the present disclosure, a method of resecting a femur bone to receive a condylar implant, which includes the step of placing an inner surface of a profiling guide against a distal portion of the femur bone. The first guide member includes a periphery dimensioned to substantially correspond to a condylar implant. The method also includes the step of adjusting the periphery of the profiling guide such that the periphery does not intersect an anteriorly resected surface and a trochlear resected surface of the femur bone. Additionally, the method includes the steps of rotating the tibia with respect to a femur along a flexion axis, and assessing a location of the inner surface of the profiling guide with respect to the anteriorly resected surface and trochlear resected surface of the femur bone.

Further, the method may include the step of coupling a distal resection guide that includes a resection slot to the profiling guide. The resection slot may be parallel to the first bone contact surface of a profiling guide and may have an axis transverse to the anterior resected surface. The method may also include the steps of coupling a posterior referencing guide to the profiling guide, and contacting a posterior portion of the femur bone with a planar surface of the posterior referencing guide.

Continuing with this aspect, the method may include the step of resecting a portion of the femur bone through the resection slot of the distal resection guide along a second distal plane parallel and offset from a first distal plane defined by the inner surface of the profiling guide to form a planar distal surface. Further the method may include the step of placing the inner surface of the profiling guide against the planar distal surface. The anterior resected surface and trochlear resected surface may define a first resected area and resecting a portion of the femur bone through the resection slot of the distal resection guide may define a second resected area such that the first resected area does not intersect the second resected area.

The profiling guide may additionally include a first resection aperture that orthogonally extends through the inner surface, and a second resection aperture that extends through the inner surface at an oblique angle with respect to the inner surface. The method may include the steps of resecting bone through the first resection aperture, and resecting bone through the second resection aperture.

BRIEF DESCRIPTION OF THE DRAWINGS

These and other features, aspects, and advantages of the present invention will become better understood with regard to the following description, appended claims, and accompanying drawings where:

DETAILED DESCRIPTION

As used herein unless stated otherwise, the term "proximal" means closer to the heart, and the term "distal" means further from the heart. The term "anterior" means toward the front part of the body or the face, the term "posterior" means toward the back of the body. The term "medial" means closer to or toward the midline of the body, and the term "lateral" means further from or away from the midline of the body. The term "inferior" means closer to or toward the feet, and the term "superior" means closer to or toward the crown of the head. The term "flexion/extension ("F/E") gap" refers to the gap formed between a femoral condyle and a surface of a proximal tibia when the knee joint is in flexion (about 90 degrees) and full extension. While the corresponding figures to the following discussion depict a resection guide in relation to a medial femoral condyle, it is noted that the following may also correspond to a lateral condyle.

Referring to FIGS. 1-4, a resection guide assembly is shown as generally including a posterior referencing guide 20, a profiling guide 30, and a distal resection guide 60. In one example, the posterior referencing guide 20 can be a spacer block guide such as the Spacer Block Handle of the Triathlon® Partial Knee Resurfacing System (Howmedica Osteonics, Mahwah, N.J.), and the distal resection guide can be the Distal Resection Guide of the Triathalon® Partial Knee Resurfacing System (Howmedica Osteonics, Mahwah, N.J.).

Figure 1:
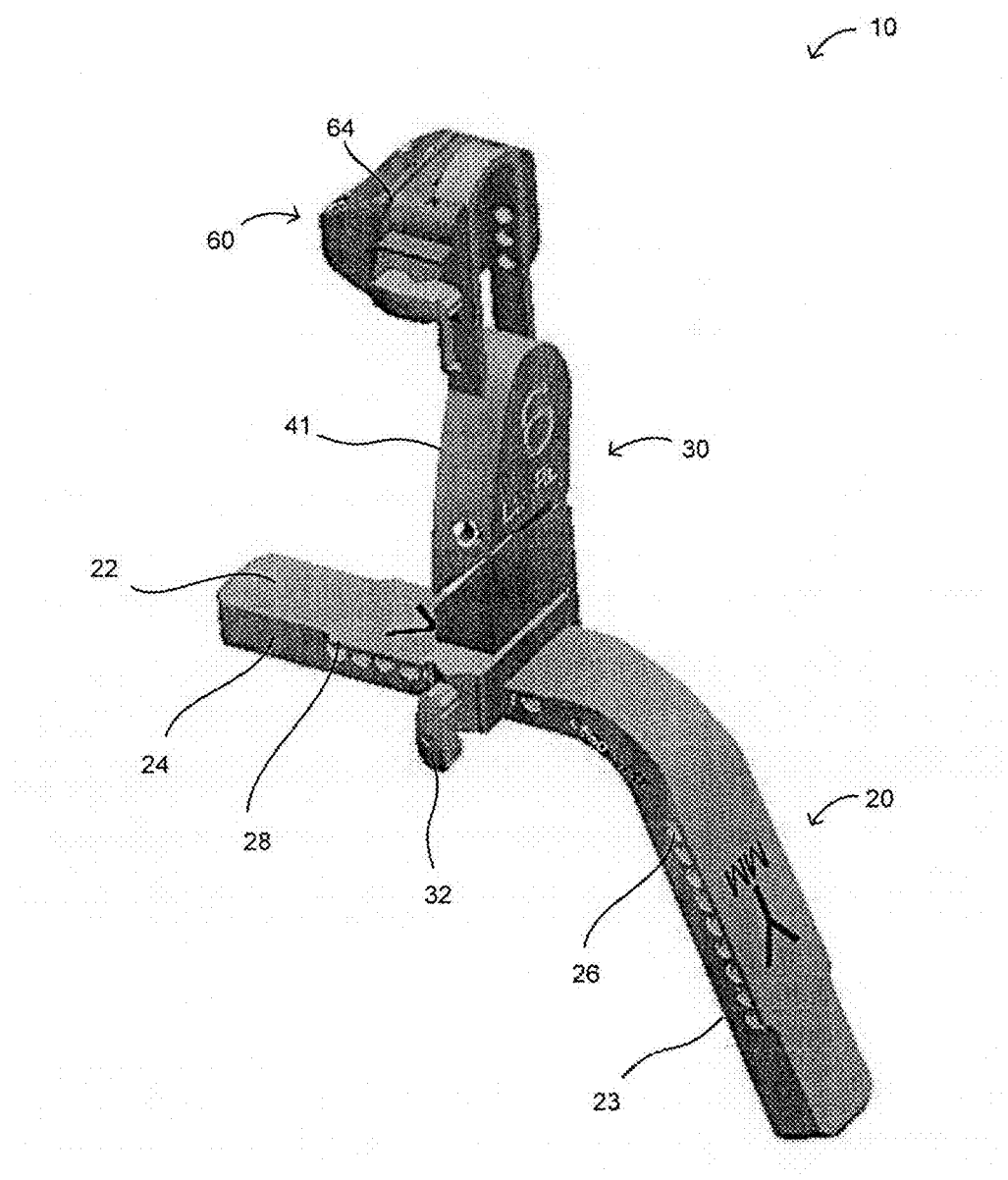
FIG. 1 is a perspective view of a resection guide assembly that includes a posterior referencing guide, a profiling guide, and a distal resection guide.

FIG. 1 depicts the posterior referencing guide 20 as having a generally rectangular cross-sectional profile and being elongate and bent about a transverse axis that is perpendicular to a longitudinal axis thereof to form a curved bar configuration that has a handle-like portion for holding posterior referencing guide 20 or for easily coupling to another instrument or guide. The rectangular cross-sectional profile defines a first or outer surface 22 and second or inner surface 23 with side surfaces or thickness 24 spanning therebetween. Extending through side surfaces 24 in a transverse direction thereto are a plurality of engagement holes 26 for receiving a locking device 32 of the profiling guide as discussed further below. The thickness 24 may be dimensioned to correspond to the dimensions of a flexion and/or extension gap. The posterior referencing guide 20 may be provided in a kit that contains multiple posterior referencing guides each having a different thickness for trialing and assessing the F/E gap.

The first surface 22 may extend beyond the boundary of the rectangular cross-sectional profile to form a stabilizing flange 28 for stabilizing and aligning the profiling guide 30 when attached to the posterior referencing guide 20 as discussed further below. Where multiple posterior referencing guides are provided in a kit, the engagement holes 26 may be distanced from the stabilizing flange 28 the same for each posterior referencing guide so that the profiling guide 30 may universally connect to each posterior referencing guide of the kit.

Figure 2:
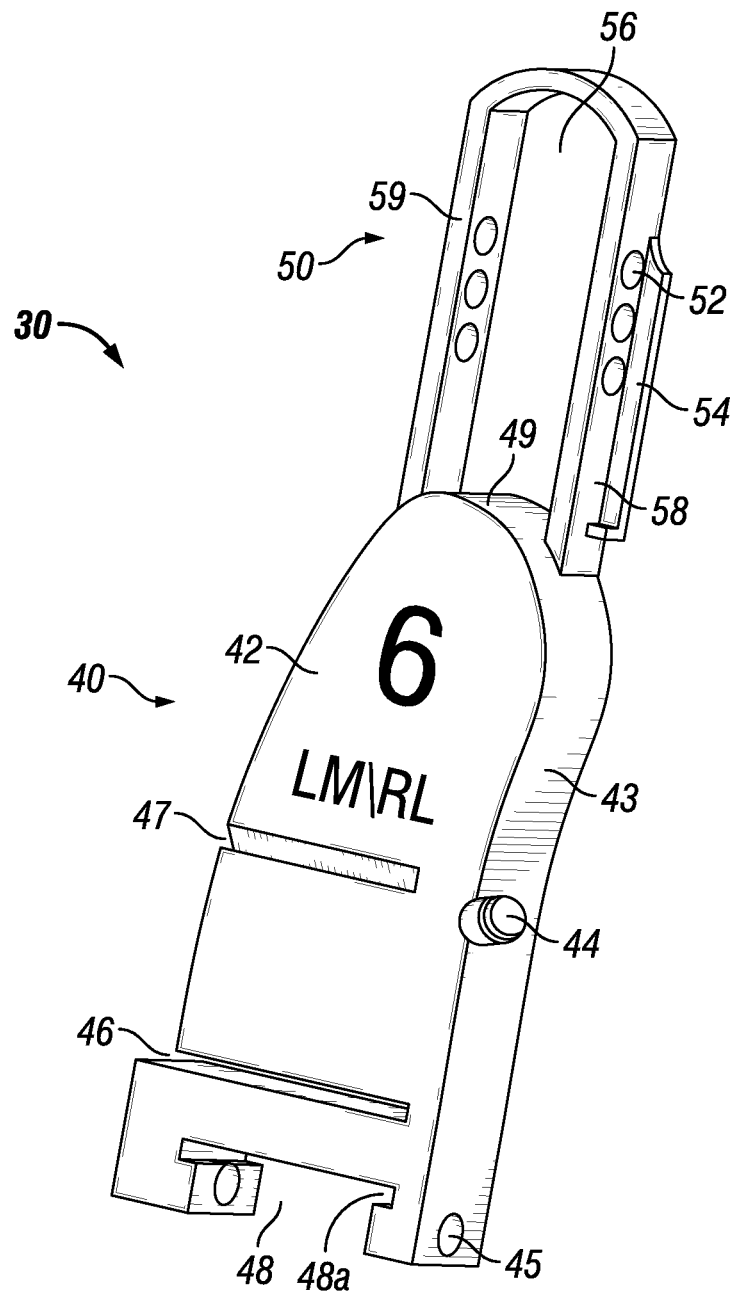
FIG. 2 is a perspective view of an embodiment of the profiling guide of FIG. 1.

As shown in FIG. 2, the profiling guide 30 generally includes a body 40 and a connector rail 50. The body 40 may include a bone contact surface 41 and an opposed surface 42 that may be disposed opposite and substantially parallel the bone contact surface 41. In some embodiments, these surfaces 41, 42 may be angled with respect to one another or the opposed surface 42 may be curved. The distance separating the bone contact surface 41 and opposed surface 42 may define the thickness of body 40 and may form an intermediate wall 43 that may orthogonally converge with the bone contact surface 41 and the opposed surface 42.

The orthogonal convergence between the intermediate wall 43 and surfaces 41, 42 may define the periphery or outline of the profiling guide 30. Further, the convergence of the bone contact 41 and opposed surface 42 with the intermediate wall 43 may occur at the outer perimeter of each of these surfaces 41, 42 and wall 43. Thus, the periphery of the body 40 may also be defined by the outer perimeter of each of these surfaces 41, 42 and wall 43, and, conversely, the outer perimeter of each of these surfaces 41, 42 and wall 43 may be defined by the periphery of the body 40. As an example, the outer perimeter of the bone contact surface 41 may be the periphery of the body 40 from one vantage point, and the outer perimeter of the intermediate wall 43 may be the periphery of the body 40 from another vantage point.

The outer perimeter of the opposed surface 42 and the bone contact/inner surface 41 may be dimensioned and geometrically configured to substantially correspond to a periphery of at least a portion of a unicondylar implant (not shown). Typically unicondylar implants have flat inner contact surfaces angled with respect to one another to engage a resected condyle and have outer surfaces that are at least partially curvilinear in the sagittal, coronal and transverse planes in order to mimic the articular surface of the distal femur bone prior to any degeneration or wear. To this extent, the bone contact surface 41, and in some embodiments the opposed surface 42, of the profiling guide 30 may be linear in the sagittal and coronal planes and planar in the transverse plane, that is, due to the planarity of the bone contact surface 41, the bone contact surface 41 may be tangent to the distal femoral condyle when in contact with the distal femoral condyle. Thus, to account for the differences between the three-dimensional implant and two-dimensional surfaces 41, 42, substantial correspondence may be achieved by dimensioning the outer perimeter of the bone contact and opposed surfaces 41, 42 as orthographic projections of at least a portion of the unicondylar implant, or close enough thereto to provide the operator an accurate picture of the periphery of the unicondylar implant.

The substantial correspondence of the peripheries may be advantageous in that a surgeon can visualize the size and location of the unicondylar implant prior to committing to a resection of the bone. Further, the linearity in the sagittal and coronal planes and planarity in the transverse plane of the bone contact surface 41 for tangentially contacting a distal femoral condyle may be advantageous in that the profiling guide 30 may be utilized as a universal instrument for various patients. In other words, due in part to the planar bone contact surface 41 of the profiling guide 30, the profiling guide 30 may be used universally with patients having varying femoral condylar geometries and varying obstructions, such as osteophytes.

In some embodiments, the profiling guide 30 may be curved to conform to the femur bone where the profiling guide is custom built using medical imaging techniques to be patient specific or is selected from a library of stock implants built for a particular population of which the patient is a part, for example. In such embodiments, osteophytes and other obstructions may be accounted for by utilizing medical imaging. However, there is a greater likelihood that such patient specific embodiment may not conform as desired when compared to profiling guide 30, in which case profiling guide 30 may be used as a contingency if needed.

The body 40 of the profiling guide 30 may also include a first and second resection apertures 46, 47, an angled pinhole 44, a first T-slot 48 and a connector hole 45. The first resection aperture 46 may extend through the opposed surface 42 and the bone contact surface 41 such that a plane defined by the aperture 46 may be orthogonal to at least the bone contact surface 41. Aperture 46 is preferably used to guide a posterior cut on the distal femur. The first resection aperture 46 may also extend orthogonally through the opposed surfaces 42 where the opposed surface 42 is substantially parallel to the bone contact surface 41.

The second resection aperture 47 may extend through the bone contact surface 41 and the opposed surface 42. Aperture 47 is preferably used to guide a posterior chamfer cut on the distal femur. A plane defined by the second resection aperture 47 may be oblique with respect to the bone contact and opposed surfaces 41, 42. This angle may be determined by the geometry of an inner surface of a unicondylar implant, for example the angle of the second resection aperture 47 may substantially correspond to an angle of a chamfer located on the inner surface of a unicondylar implant.

As shown in FIG. 2, the first and second resection apertures 46, 47 may extend through the intermediate wall 43 at one location. However, in some embodiments these apertures 46, 47 may not extend through the intermediate wall 43 and may only extend through the bone contact and opposed surfaces 41, 42. In other embodiments, the first and second resection apertures 46, 47 may not extend through the opposed surface 42 but may extend through the intermediate wall 43 and the bone contact surface 41, thereby facilitating a bone cutting device to enter through the intermediate wall 43, rather than the opposed surface 42.

The angled pinhole 44 may also extend through the intermediate wall 43 and through the bone contact surface 41 but may not extend through the opposed surface 42. However, in some embodiments the angled pinhole 44 may extend through the opposed surface 42, the intermediate wall 43 and the bone contact surface 41. And in other embodiments the angled pinhole 44 may only extend through the opposed surface 42 and bone contact surface 41. This pinhole 44 may be obliquely angled with respect to the bone contact surface 41 so that a pin extending therethrough and into a femur can oppose movement of the profiling guide 30 in multiple directions.

The first T-slot 48 may extend through one end of the body and may have a "T" shaped configuration that may include a cross-slot portion 48a. The cross-slot portion 48a may be dimensioned to slidably receive the stabilizing flange 28 of the posterior referencing guide 20, while the remaining portion of the first T-slot 48 may be dimensioned to receive the thickness 24 of the posterior referencing guide 20. A connector hole 45 may extend through each side of the first I-slot 48 so that the locking mechanism 32, for example a spring loaded connector, can pass through the hole 45 and engage an engagement hole 26 of the posterior referencing guide 20.

The connector rail 50 is preferably coupled to and extends from the other end of the body 40 such that a longitudinal axis of the connector rail 50 is substantially parallel to the bone contact surface 41. However, in some embodiments, the longitudinal axis of the connector rail 50 may be angled with respect to the bone contact surface 41. The connector rail 50 may be u-shaped and have a first leg 58 and second leg 59 coupled to the body 40 at two points to form a viewing window 56 therebetween. The connector rail 50 may be substantially thin and be coupled to the body 40 at locations away from the apex 49 of the body 40 so that the operator has an unobstructed view through the viewing window of the periphery at an apex 49 to help facilitate an accurate depiction of possible impingement with a patellofemoral implant.

The first and second legs 58, 59 of the connector rail 50 may include an alignment flange 54 and a plurality of retainer holes 52 extending through each leg 58, 59 or through either leg 58 or leg 59 and into the viewing window 56. In some embodiments, the retainer holes 52 may not extend entirely through each leg 58, 59, but may be a circular recess extending partially into each leg 58, 59. These flanges 54 and holes 52 may be configured similarly to the stabilizing flange 28 and engagement holes 26 of the posterior referencing guide 20 so that the distal resection guide 60 may connect to both the posterior referencing guide 20 and profiling guide 30 in substantially the same way.

Figure 3A:
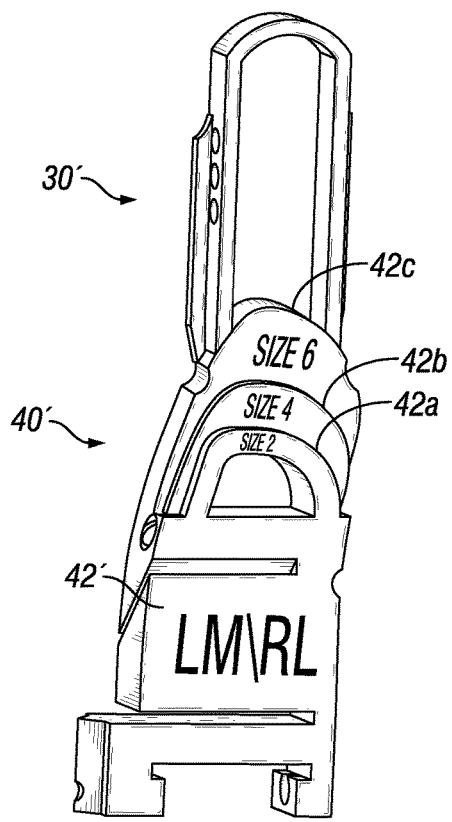
FIG. 3A is a perspective view of another embodiment of the profiling guide of FIG. 1.
Figure 3B:
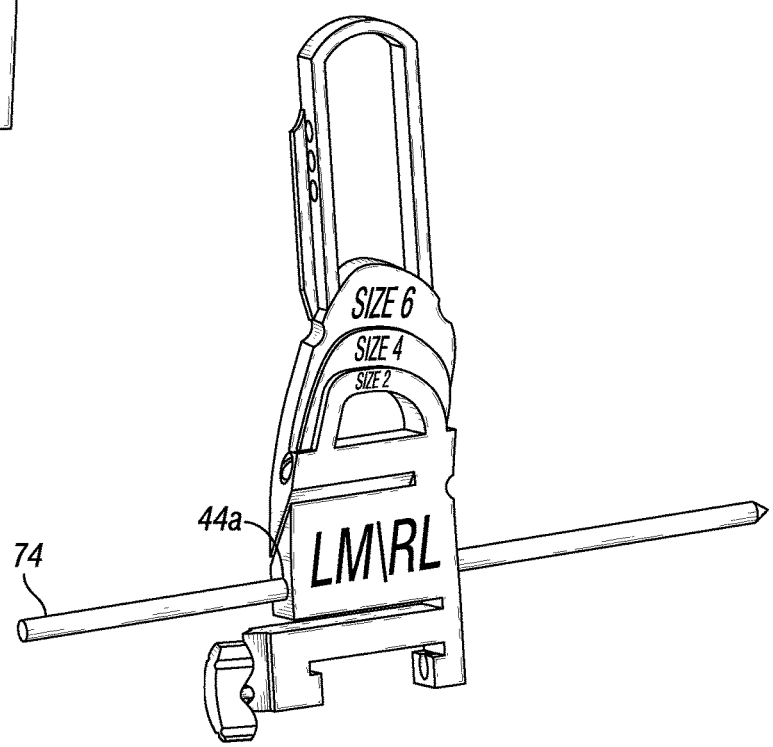
FIG. 3B is a perspective view of profiling guide of FIG. 3A including at least one transverse pinhole and at least one alignment pin.

FIGS. 3A and 3B depict another embodiment of the profiling guide that is substantially similar to the profiling guide 30 of FIG. 2, but may differ in the configuration of the opposed surface 42. The body 40' of the profiling guide 30' similarly includes a bone contact surface 41 and opposed surface 42' that have outer perimeters that may define and may be defined by the periphery of the body 40' which substantially corresponds to a unicondylar implant. Additionally, the opposed surface 42' may include at least one periphery or outline that has a perimeter that may substantially correspond to a periphery of a unicondylar implant that is of a smaller size than that which corresponds to the periphery of the body 40'. As an example, FIGS. 3A and 3B show a profiling guide 30' that includes two outlines 42a and 42b that substantially correspond to a size 2 and a size 4 unicondylar implant, respectively, and the outer perimeter 42c of the bone contact and opposed surfaces 41, 42' that substantially corresponds to a size 6 implant. These outlines 42a and 42b may be machined or laser-etched into the opposed surface 42', or may be formed by any other method known in the art.

FIG. 3B depicts the profiling guide as including a transverse pinhole 44a for receiving an alignment pin 74 for alignment with a boney landmark such as the epicondylar axis, distal condylar axis, or posterior condylar axis, for example. This transverse pinhole 44a extends through the intermediate wall 43 and may be included in either the first or second embodiment 30, 30' of the profiling guide. In some embodiments, this pinhole 44a may be two pinholes that are situated along the same axis, but do not extend entirely through the profiling guide 30 or 30'. Thus, one or two alignment pins may be utilized in such embodiments.

A profiling guide 30' that has an opposed surface 42' with at least one outline of a corresponding smaller unicondylar implant may provide certain advantages. One such advantage may be that the outlines 42*a*, 42*b* combined with the periphery of the body 40' may allow the operator to simultaneously evaluate the femur for the most appropriate sized implant and align the resection guide assembly 10 in view of the most appropriate size to avoid impingement with an anterior resected surface and trochlear resected surface intended for a patellofemoral implant.

Figures 4, 5:
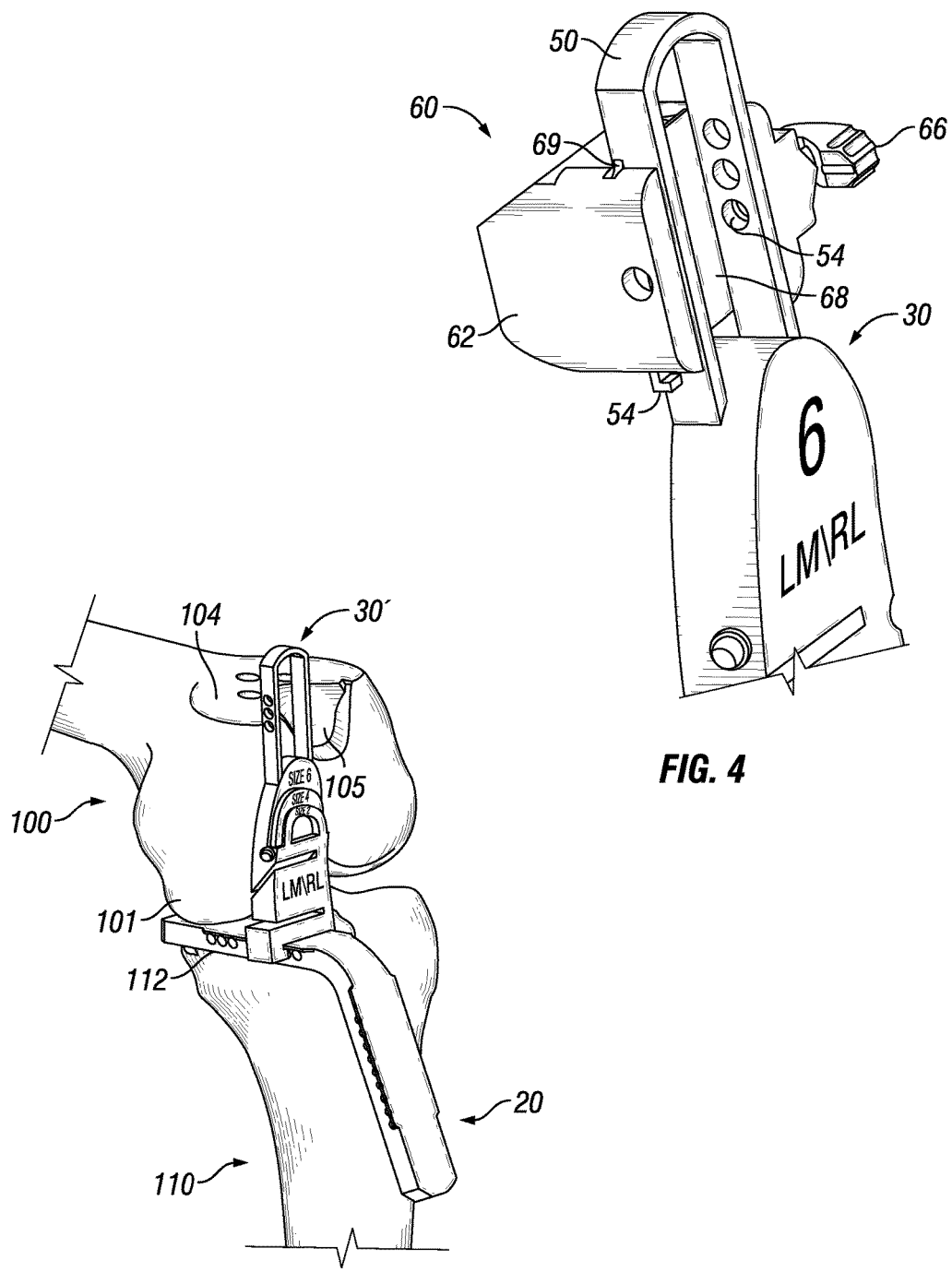
FIG. 4 is a perspective view of the distal resection guide connected to the profiling guide of FIG. 2.
FIG. 5 is a perspective view of the posterior referencing guide of FIG. 1 positioned within a flexion gap between a tibia and a posterior femoral condyle, and the profiling guide of FIG. 3A positioned against a distal femoral condyle.

The distal resection guide 60 as depicted in FIGS. 1 and 4 may include a guide body 62, a third resection aperture or distal resection slot 64, at least one pinhole (not shown), a locking mechanism 66 and a second T-slot 68. The second T-slot 68 may extend through a portion of the guide body 62 and may be substantially similar to the first T-slot 48 of the profiling guide 30 so that the distal resection guide 60 may be connected to either the connecting rail 50 of the profiling guide 30 or the posterior referencing guide 20. A locking mechanism 66, such as a spring loaded connector, may selectively extend through guide body 62 and into the second T-slot and for engaging either a retainer hole 54 of the profiling guide 30 or an engagement hole 26 of the posterior referencing guide 20.

One or more pinholes may extend through the guide body 62 at various angles so that the distal resection guide 60 may be temporarily anchored to the bone during a distal resection. These pinholes are generally oriented so that a pin inserted therethrough would not obstruct a cutting device extending through the distal resection slot 64.

The distal resection slot 64 extends through the guide body 62 such that a plane defined by the distal resection slot 64 is preferably substantially parallel to the bone contact surface 41 when the distal resection guide 60 is connected to the connector rail 50. In other embodiments, the plane defined by the distal resection slot 64 may be angled with respect to the bone contact surface 41 when the distal resection guide 60 is connected to the connector rail 50. The distance of the second T-slot 68 to the distal resection slot 64 may be determined by the desired amount of bone to be removed.

Generally, when the distal resection guide 60 is attached to the profiling guide 30 and a cutting device is extended through the distal resection slot 64, the cutting device may penetrate a femur at a location projected from the apex 49 of the body 40. Thus, an operator viewing the apex 49 at eye-level with respect to a femur may be provided an accurate depiction of the location in which the cutting device may penetrate the femur. This location may vary depending on the curvature of the condyle and the desired amount of bone to be removed. Such variations may be small enough to provide the operator with accurate information in order to avoid impingement.

In one embodiment of the resection guide assembly 10, the profiling guide 30 may be slidably connected to the posterior referencing guide 20 as depicted in FIG. 1. In such a configuration, the stabilizing flange 28 may engage the cross-slot portion 48*a* of the T-slot 48, which may provide rotational stability and alignment of the profiling guide 30 with respect to the posterior referencing guide 20.

The profiling guide 30 may be connected in an orientation with respect to the posterior referencing guide 20 such that a first plane defined by the first surface 22 of the posterior referencing guide 20 may orthogonally intersect a second plane defined by the bone contact surface 41 of the profiling guide 30. The slidable connection allows for the length of the posterior referencing guide 20 in contact with the tibia to be adjusted to accommodate tibias of varying size. In another embodiment, the profiling guide 30 and posterior referencing guide 20 may be integrally connected to form a monolithic structure.

The orthogonal intersection/connection may provide certain advantages. One such advantage may be to assist in F/E gap balancing. In this orthogonal orientation, the posterior referencing guide 20 may contact the most posterior aspect of the femoral condyle and the profiling guide 30 may contact the most distal aspect of the femoral condyle at a given angle of flexion. This may allow the depth of the distal resection to remove the desired amount of distal bone with respect to the posterior bone for balancing the F/E gap.

The distal resection guide 60 may be slidably connected to the profiling guide 30 in a similar manner. This slidable engagement may allow the distal resection guide 60 to be set at differing heights from the body 40 in order to accommodate femurs of differing sizes. The distal resection guide 60 may be connected to the connector rail 50 so that the alignment flange 54 may pass into a cross-slot section 69 of the second T-slot 68. This may provide rotational stability and alignment to the distal resection guide 60 with respect to the profiling guide 30 to ensure proper alignment between the bone contact surface 41 and the distal resection slot 64. Additionally, the locking device 66 may pass through one of the retainer holes 54 to lock the distal resection guide into position at a desired height.

Referring to FIGS. 5-14, a method for forming a femoral condyle 100 to receive a unicondylar implant is depicted. The following method is described with the presumption that a patellofemoral arthroplasty has been performed prior to the herein described method. However, it is noted that the following described method may be advantageous where a patellofemoral arthroplasty is performed after the method, or where a patellofemoral arthroplasty is not performed at all, that is, where only a unicondylar arthroplasty is desired.

A patellofemoral arthroplasty typically resects an anterior portion of a distal femur and a distal portion of the femur, more specifically the trochlear groove. An example of an anterior resection and trochlear resection can be found in U.S. Provisional Application No. 61/768,765, the disclosure of which is hereby incorporated by reference herein in its entirety. This anterior resection 104 and trochlear resection 105 is generally made to clear a space for a patellofemoral implant and defines a first resected area. It is desirable to avoid impinging on the anterior resection 104 and trochlear resection 105 when forming a femoral condyle 100 to receive a unicondylar implant for various reasons including the avoidance of removing supporting bone for the patellofemoral implant. The following method may be utilized to avoid such impingement.

Once the patellofemoral joint has been prepared to receive a prosthesis, the tibiofemoral joint may be prepared in accordance with the following method. Generally, a portion of the tibial plateau may be resected in order to replace the articular surface of the tibia 110. This proximal resection 112 may be guided by use of an ankle clamp, an example of which can be found disclosed in U.S. Pat. No. 8,377,069, for example.

Thereafter, the F/E gap may be assessed to determine the amount of bone to be resected from the femoral condyle 100 in order to ensure joint stability through the arc of motion from full extension through deep flexion. F/E gap assessment may be achieved by inserting the posterior referencing guide 20 with a known thickness between the distal femoral condyle 102 and resected proximal tibia 112, and the posterior femoral condyle 101 and resected proximal tibia 112 in order to assess soft tissue tension relative to the known gap thickness. The operator may then choose a distal resection guide 60 based on the F/E gap assessment for removal of a desired amount of bone from the distal aspect 102 of the femoral condyle.

Figures 6, 7:
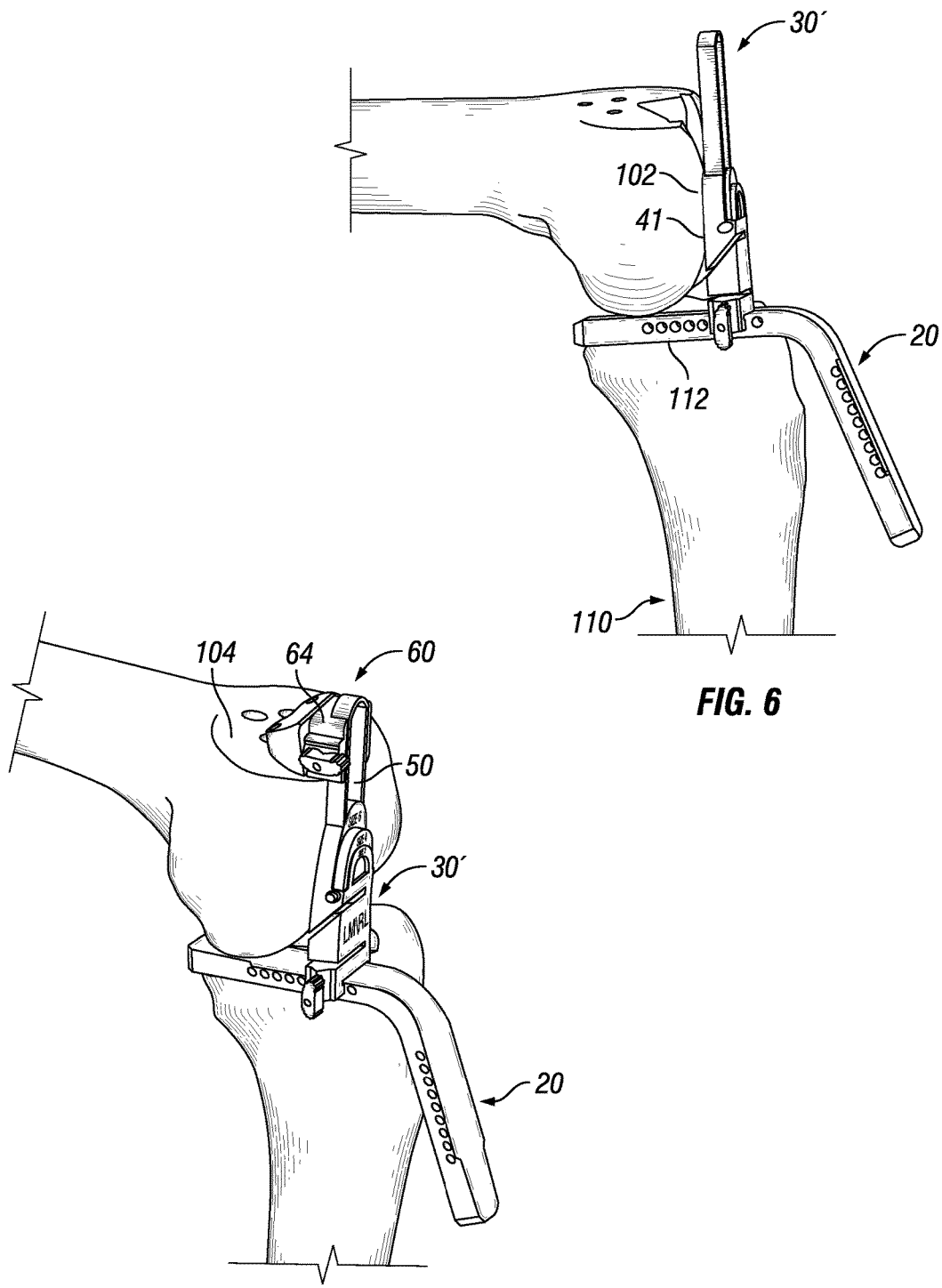
FIG. 6 is a side view of the configuration of FIG. 5.
FIG. 7 is a perspective view of the assembly shown in FIG. 5 including a distal resection guide positioned against an anterior surface of the femur.

Referring to FIGS. 5 and 6, the profiling guide 30' may thereafter be assembled to the posterior referencing guide 20 by sliding the posterior referencing guide 20 through the T-slot 48 of the profiling guide 30'. While the knee joint is in flexion of about 90 degrees, the posterior referencing guide 20 may be inserted into the flexion gap and into contact with the resected proximal tibia 112 and the most posterior aspect of the femoral condyle 100. Adjustment of flexion and tibial rotation of the knee can be performed so that the first surface (not shown) of the posterior referencing guide 20 rests flat against the resected proximal tibia 112, while the second surface 22 tangentially contacts the posterior condyle 101. The profiling guide 30' may be slid into contact with the most distal aspect of the femoral condyle 100 so that the bone contact surface 41 is generally tangent to the distal condyle 102.

Referring to FIG. 7, the distal resection guide 60 selected via F/E gap assessment may be attached to the profiling guide 30' as shown. The distal resection guide 60 may be slid over the connecting rail 50 of the profiling guide 30' until the distal resection guide 60 contacts an anterior surface of the distal femur.

Referring to FIGS. 8-13B further assessments and adjustments may be made to align the profiling guide 30' with the distal femoral condyle 102 in representation of a unicondylar implant. This may be an iterative process of assessing the profiling guide's alignment with respect to boney landmarks, assessing the distal resection for impingement with the anterior resection 104 and trochlear resection 105, assessing the profile of the profiling guide 30' with respect to the femoral condyle for an overall prediction of the location of the final implant, and moving the resection guide assembly 10 to adjust based on these assessments.

Generally, this iterative process may be utilized to first orient and locate the distal condylar resection such that the varus-valgus angle of the distal resection is as desired and such that the distal resection does not impinge on the anterior resection 104 and trochlear resection 105. Once the distal resection is performed, the iterative process may then be utilized to align internal-external rotation for a posterior and chamfer resection.

Figure 8:
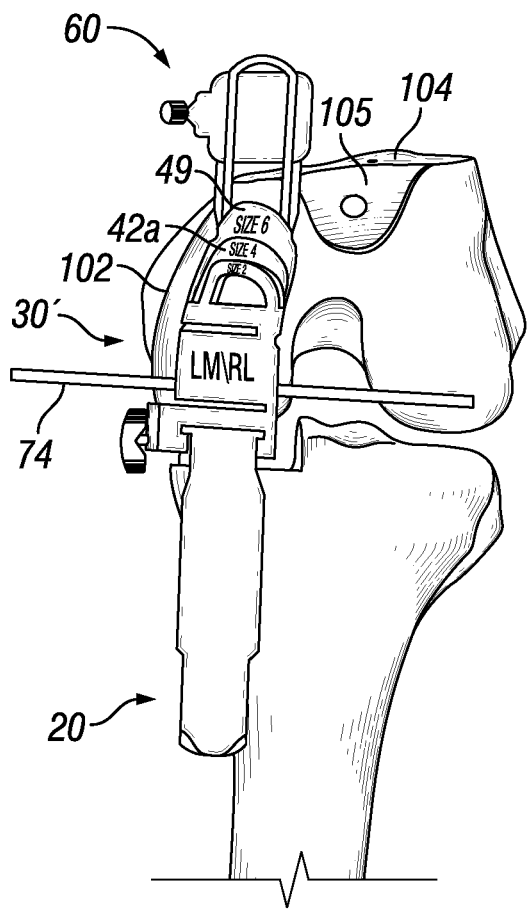
FIG. 8 is front view of the assembly shown in FIG. 7 including an alignment pin(s).
Figure 9A:
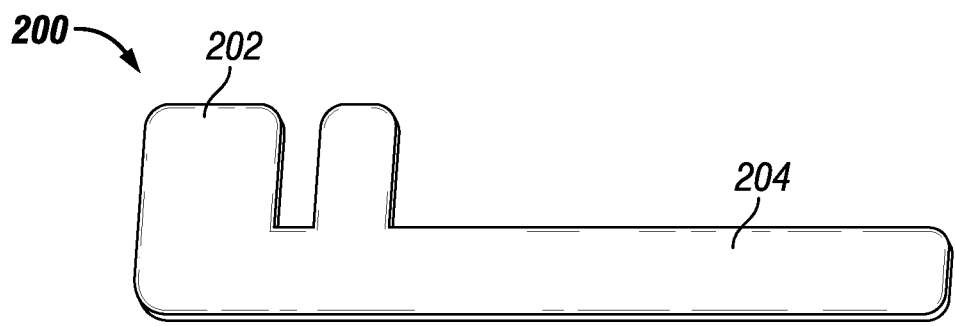
FIG. 9A is a perspective view of one embodiment of an alignment shim.
Figure 9B:
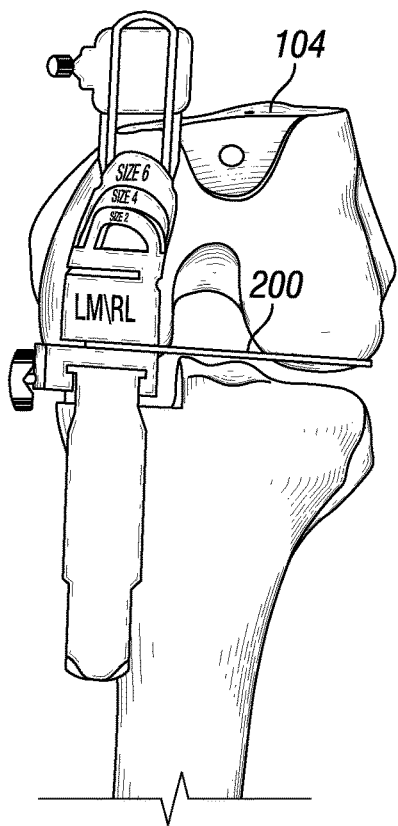
FIG. 9B is a front view of the assembly shown in FIG. 7 including the alignment shim of FIG. 9A.
Figure 9C:
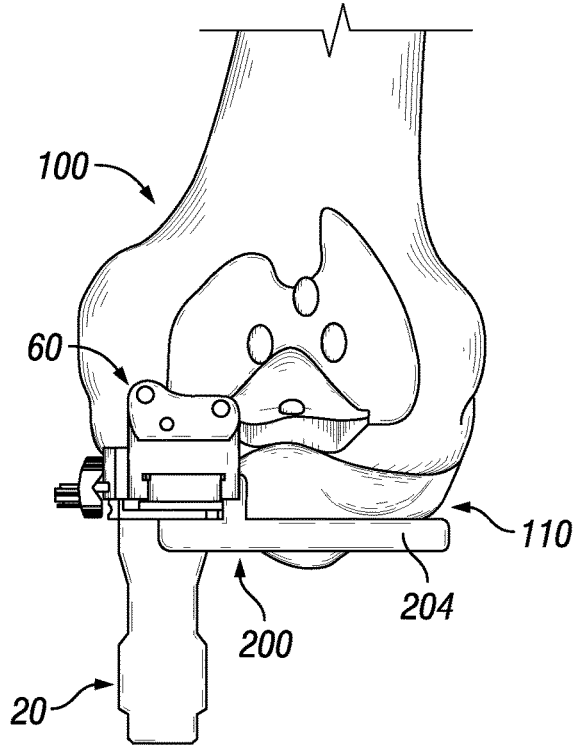
FIG. 9C is a top view of the assembly shown in FIG. 9B.

FIGS. 8-9C illustrates assessment and alignment with one or more boney landmarks, such as the epicondylar axis, distal condylar axis and posterior condylar axis, for example. Alignment with boney landmarks is optional, but may facilitate a more natural final implant location. Referring to FIG. 8, an alignment pin 74 may be inserted through the transverse pinhole 44a. With the knee joint generally at 90 degrees of flexion, the operator may view the alignment of the alignment pin 74 with respect to a boney landmark to assess varus-valgus and/or internal-external rotational alignment of the profiling guide 30' with respect to the femoral condyle. An alternative to the alignment pin 74 is illustrated in FIGS. 9A-9C. FIG. 9A depicts an alignment shim 200 that is sized to be slid into the first resection aperture 46 of the profiling guide 30' and includes a forked end 202 to engage the profiling guide 30' to help provide stability and ensure proper orientation of an alignment end 204. Similar to the alignment pin 74, the alignment end 204 and first resection aperture 46 may be used to visualize alignment with a bony landmark.

An example of bony landmark alignment is illustrated in FIG. 9C, which depicts varus-valgus alignment. Varus-valgus alignment, which sets the varus-valgus angle of the distal condylar resection, may generally be achieved where the longitudinal axis of the alignment end 204 of the alignment shim 200 (alternatively, the longitudinal axis of the alignment pin 74) is parallel with the epicondylar axis or distal condylar axis when viewing the femur and alignment shim 200 in an anteroposterior direction. Where alignment is not visualized, the posterior referencing guide 20 may be manipulated to rotate the assembly 10 about the tibial shaft axis while maintaining contact with the posterior condyle until alignment is achieved.

FIGS. 10A-12C depict assessment and alignment of the distal resection with respect to the anterior and trochlear resections 104, 105 in order to avoid impingement and also depicts overall assessment of the final implant location. Adjustments may be made to avoid impingement and locate the optimum location for the final implant by rotating the tibia 110 in flexion or extension to adjust the positioning of the profiling guide 30' posteriorly or anteriorly, respectively, with respect to the femur. As the tibia 110 is rotated, the first surface of the posterior referencing guide 20 may remain flat against the proximal resected surface 112, thereby moving the profiling guide 30' along the distal condyle 102 posteriorly or anteriorly as desired.

Figure 10C:
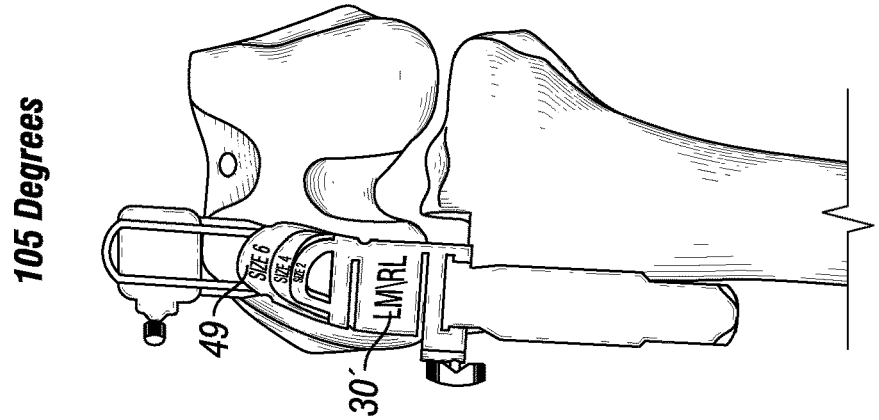
FIGS. 10A-C are front views of the assembly shown in FIG. 7 with the knee joint in 75, 90 and 105 degrees of flexion, respectively.
Figure 10B:
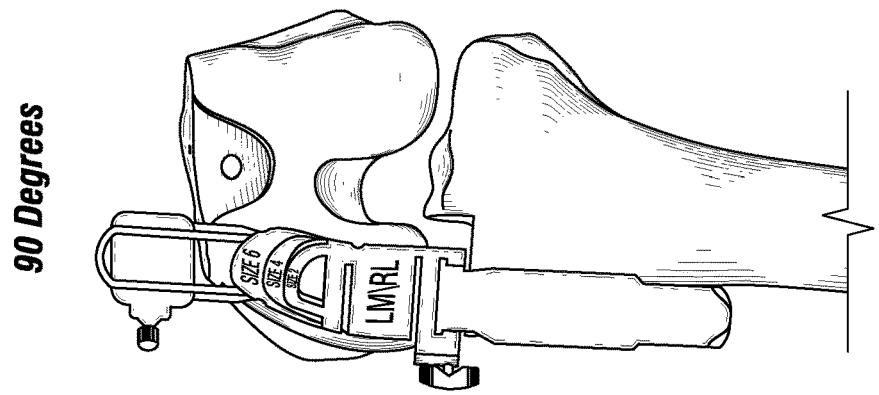
Figure 10A:
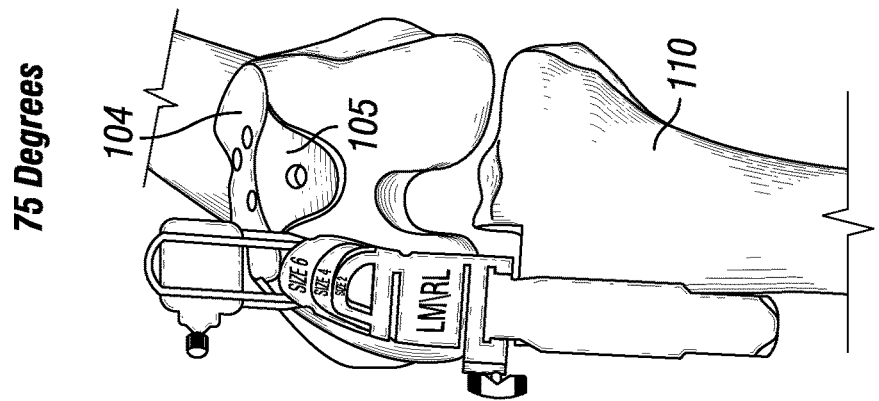

FIGS. 10A-C depict the profiling guide 30' in relation to a femoral condyle where the knee joint is in 75, 90, and 105 degrees of flexion to illustrate that the operator may utilize the outer perimeter of the bone contact and opposed surfaces 41, 42 to accurately visualize the location in which the unicondylar implant may be implanted. Additionally, the operator may use these perimeters to visualize potential impingement with the anterior resection 104 and trochlear resection 105 by viewing the apex 49 and outer perimeter of the profiling guide 30' at roughly eye-level with respect to the distal condyle 102, anterior resection 104, and trochlear resection 105. Where the line-of-sight intersects the apex 49 and anterior resection 104 and/or intersects the perimeter and trochlear resection 105, there may be a risk of impingement. In the event impingement is visualized, the tibia 110 may be rotated in flexion to move the profiling guide 30' posteriorly until the risk of impingement is reduced. Conversely, where a large distance between the apex 49 of the profiling guide 30' and the anterior resection 104 is visualized, the operator may rotate the tibia 110 in extension, thereby moving the profiling guide 30' anteriorly into a desired position.

Where the profiling guide 30' includes outlines to represent unicondylar implants of various sizes as shown in FIGS. 10A-C, the operator may select a particular size unicondylar implant based on his or her assessment of the relative size of the femur and unicondylar implant's periphery as represented by the profiling guide 30' with respect to the distal condyle 102. Further, the operator may utilize these outlines to align the profiling guide 30' with respect to the distal condyle 30' to avoid impinging on the anterior resection 104 and trochlear resection 105.

Where a profiling guide 30 is provided in a kit of profiling guides that each have peripheries of different dimensions to match different sized unicondylar implants, the operator may remove and replace the profiling guide 30 with other profiling guides until the desired size is determined. The desired size profiling guide 30 may then be utilized in the same manner as described above to align the profiling guide 30 to avoid impingement.

Figure 11C:
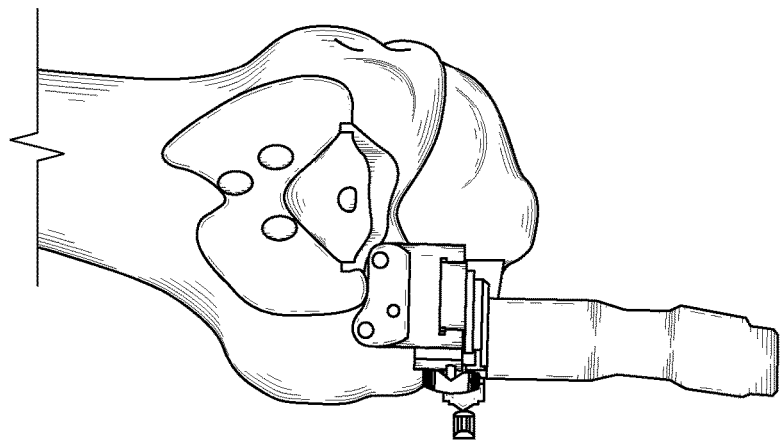
FIGS. 11A-C are top views of the assembly shown in FIG. 7 with the knee joint in 75, 90 and 105 degrees of flexion, respectively.
Figure 11B:
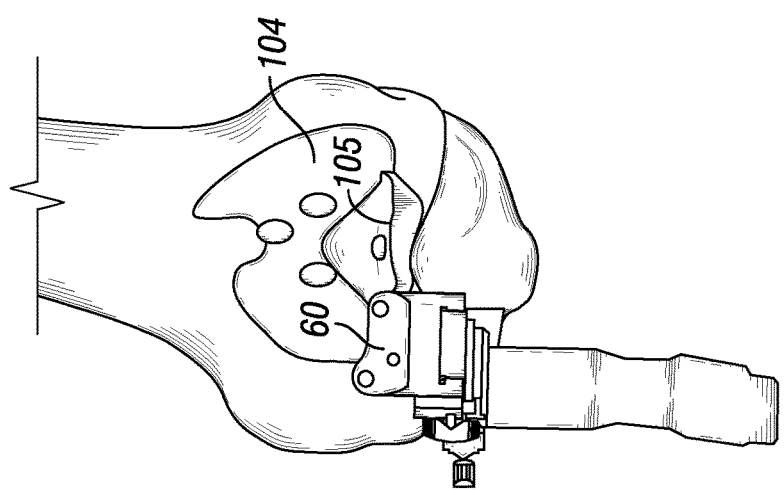
Figure 11A:
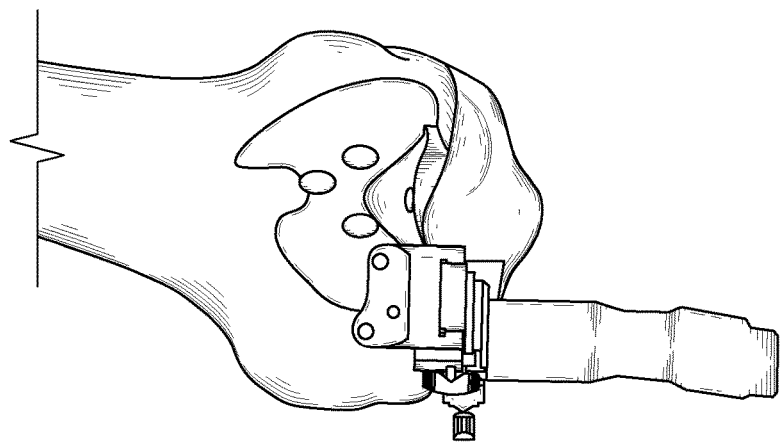
Figure 12C:
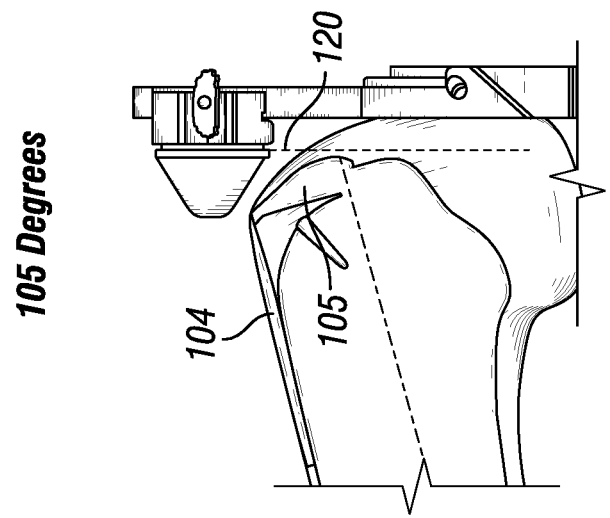
FIGS. 12A-C are sagittal cross-sectional views of a distal femur taken through the trochlear groove thereof, including the assembly of FIG. 7 with the knee joint in 75, 90 and 105 degrees of flexion, respectively.
Figure 12B:
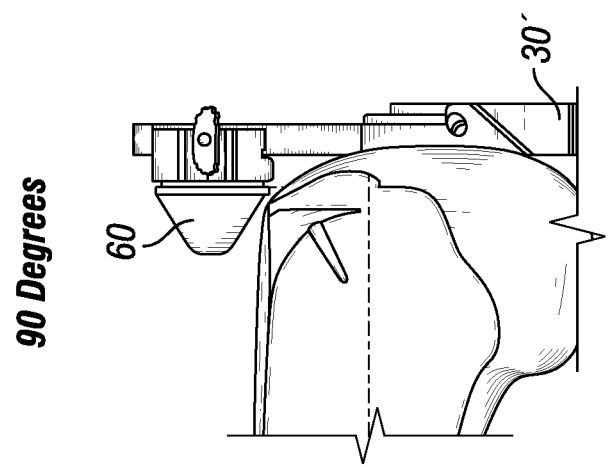
Figure 12A:
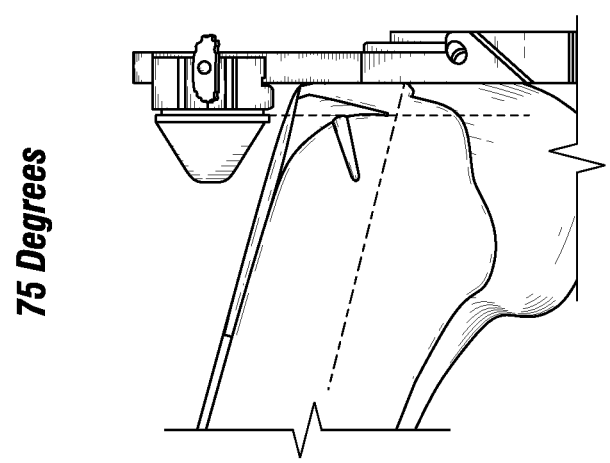

Additional visualization may be used to assess and avoid impingement with the anterior resection 104 and trochlear resection 105. Where a plane 120 defined by the distal resection slot 64 impinges with the anterior resection 104 and/or trochlear resection 105, the tibia 112 may be rotated in flexion to move the profiling guide 30' posteriorly until the risk of impingement is resolved. Impingement may be determined by viewing the distal resection slot 64 from an anterior-posterior direction as depicted in FIGS. 11A-C and a medial or lateral direction as depicted in FIGS. 12A-C to assess the location of the distal cut with respect to the anterior resection 104 and trochlear resection 105. Thus, a distal resection slot 64 that extends through a side portion of the guide body 62 may be beneficial in aiding the visualization of the resection line.

Figure 13A:
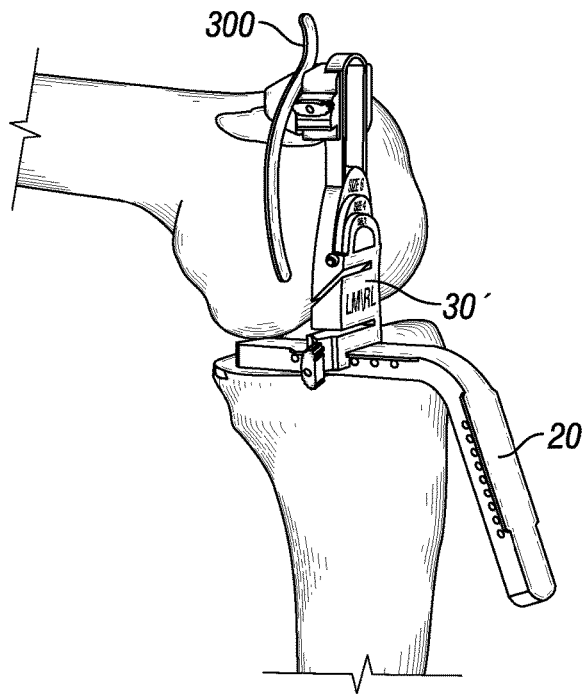
FIG. 13A is a perspective view of the assembly shown in FIG. 7 including one embodiment of a blade runner demonstrating a distal resection run-out.
Figure 13B:
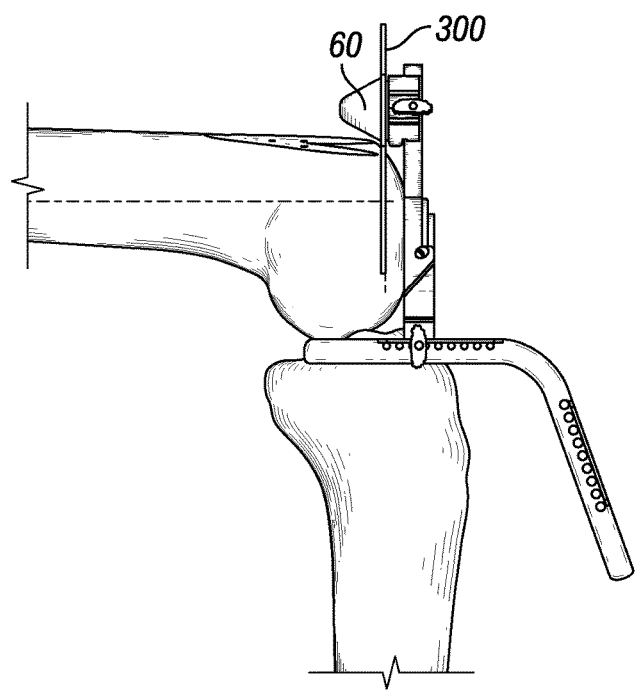
FIG. 13B is a side view of FIG. 13A.

FIGS. 13A and 13B illustrate a blade runner 300 that may be optionally used to visualize the distal resection. The blade runner 300 may be sized to fit within the distal resection slot 64 and may be curved to avoid interference with the condyle and/or osteophytes. The blade runner 300 may be inserted into the distal resection slot 64 such that the axis of the blade runner extends posteriorly. FIGS. 12A-C, depict plane 120 defined by the distal resection slot 64 with respect to the anterior resection and trochlear resection when the knee joint is at 75, 90, and 105 degrees, respectively. The axis of the blade runner 300 may align with this plane 120 providing the operator a physical element to more precisely visualize the distal resection location and any potential impingement. As described above, if impingement is visualized, the knee may be flexed into a deeper angle of flexion to avoid impingement.

Figure 14:
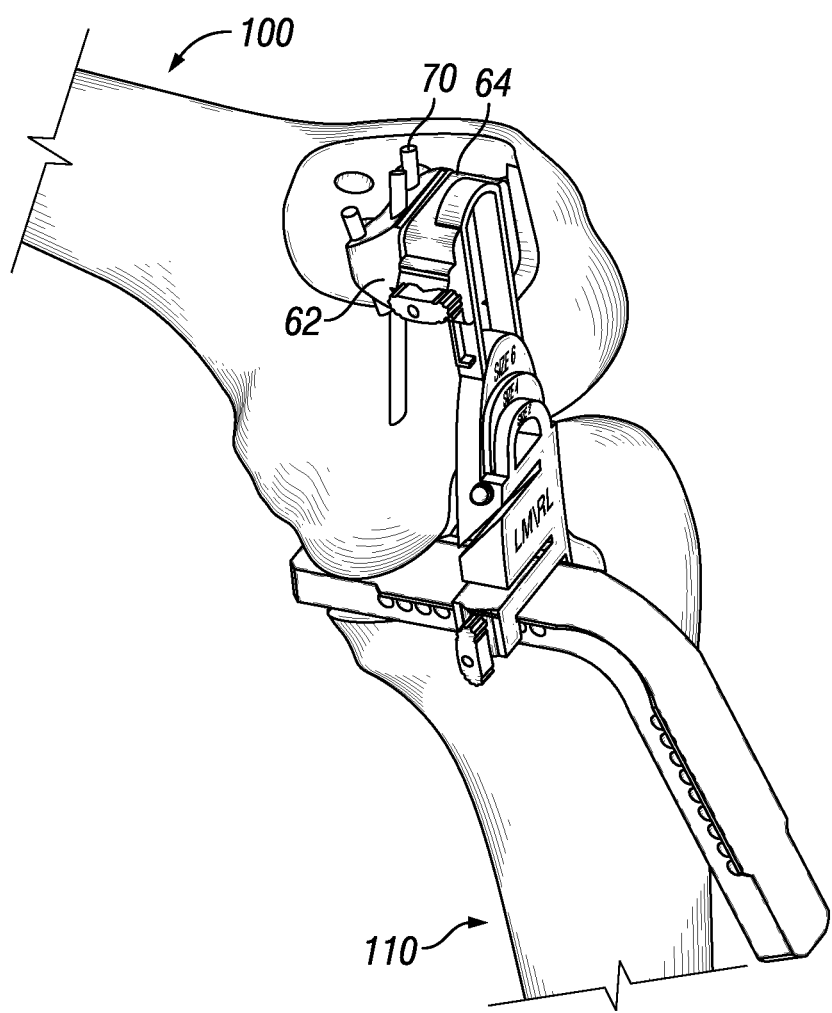
FIG. 14 is a perspective view of the assembly shown in FIG. 7 with the distal resection guide pinned to the femur.

Referring to FIG. 14, once the desired positioning has been achieved, the distal resection guide 60 may be pinned into position by inserting retaining pins 70 through the pinholes that extend through the guide body 62. The posterior referencing guide 20 and profiling guide 30' may then be removed or left in place during the distal resection.

Figure 15:
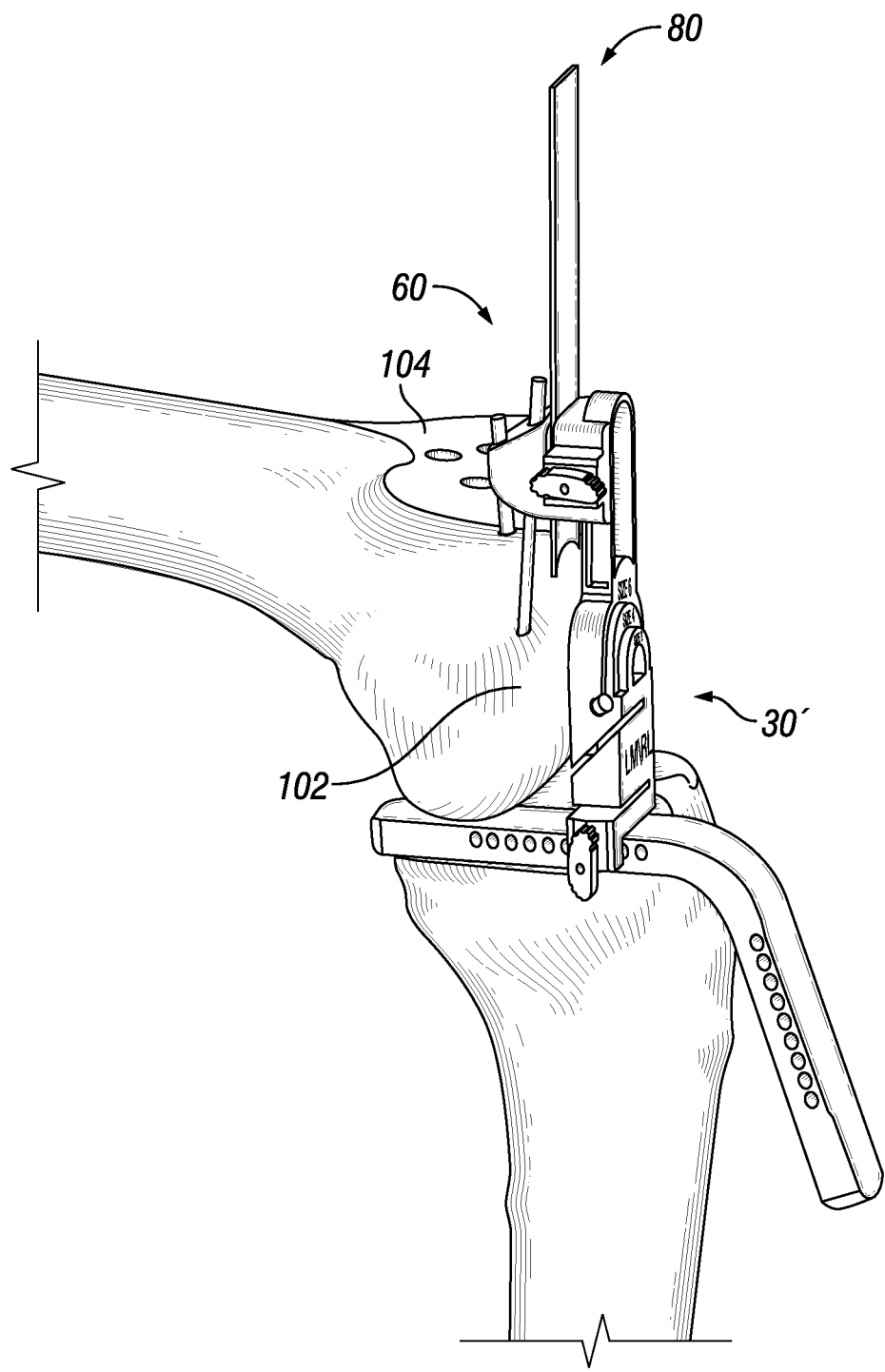
FIG. 15 is a perspective view of the assembly shown in FIG. 14 including a cutting device extending through the distal resection guide into the femur to form a distal resected surface.
Figure 16:
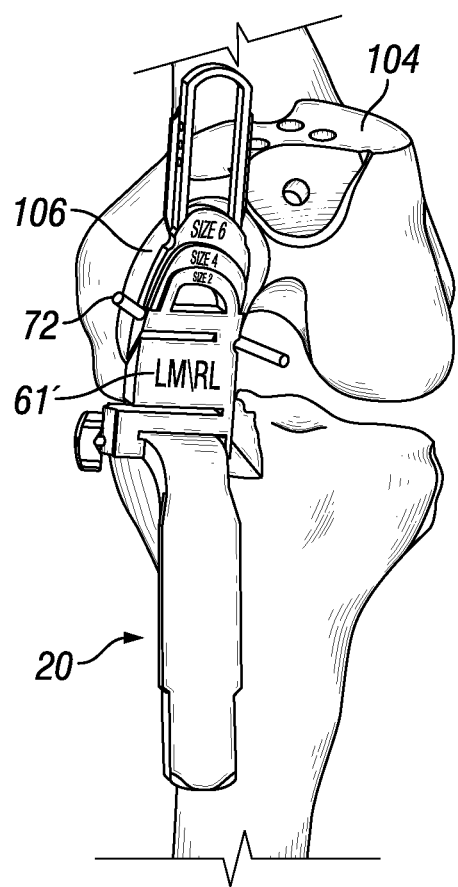
FIG. 16 is a perspective view showing the assembly of FIG. 5 with the profiling guide pinned to the distal resected surface.

As shown in FIG. 15, the distal resection may then made by inserting a bone cutting device 80 through the distal resection slot 64 along the plane formed by the distal resection slot 64 and into the bone. The distal resection may be performed while the knee joint is in flexion at roughly 90 degrees, but more precisely at an angle determined by the alignment posteriorly or anteriorly of the profiling guide 30' to avoid impingement.

Performing the distal resection while the knee joint is in flexion provides certain advantages. One such advantage is that the operator may be able to visualize where the resection will take place by viewing the distal resection slot 64 in relation to the distal condyle 102 and anterior resected surface 104 and 105 as previously described. Certain current resection guides are configured so that the distal resection is performed while the knee is in full extension, which makes visualization difficult. Generally, during a surgical procedure, when the knee is placed into extension, the femur retracts into the incision obstructing much of the lateral and medial portions of the femur making lateral and medial visualization difficult of the distal resection slot 64 in relation to the anterior resected surface 104 difficult.

Thus, at least two aspects of the resection guide assembly 10 may be beneficial in preventing impingement between the anterior resection and distal resection, namely visualization of the seated location of the unicondylar implant via visualization of the periphery of the profiling guide 30' with respect to the distal femoral condyle 102, and the ability to make the distal resection while the knee joint is in a position of flexion.

Another advantage of making the distal resection while the knee joint is in flexion is that the posterior referencing guide 20 can act as a depth stop against bone cutting device excursion. Where the distal resection is performed while the knee is in full extension, typically no structure is positioned to block the bone cutting device 80 in the event of posterior excursion. Such excursion can cause damage to many soft tissue structures located in the popliteal. Conversely, where the posterior referencing guide remains positioned in the flexion gap during the distal resection, posterior excursion may be blocked by the posterior referencing guide 20. Further, where the posterior referencing guide 20 is removed prior to the distal resection, the susceptible structure to posterior excursion may be the tibia, which is less sensitive than the popliteal to problematic damage.

Additionally, performing the distal resection while the knee joint is in flexion aids in moving the medial collateral ligament and lateral collateral ligament and other such soft tissue structures to prevent damage in the event of excursion in a lateral or medial direction.

Referring to FIGS. 16-19, once the resected bone is removed, the distal resection guide 60 may be unpinned and removed. The posterior referencing guide 20 may then be inserted back into the flexion gap where the posterior referencing guide 20 and profiling guide 30' were removed prior to a distal resection 106 defining a second resected area. The profiling guide 30' may be slid into contact with the distal resected surface 106 such that the bone contact surface 41 is flat against the distal resected surface 106.

With the profiling guide 30' contacting the distal resected surface 106, internal-external rotational alignment of the profiling guide 30', and more specifically the first and second resection apertures 46, 47, may be assessed. Assessment of internal-external rotation may be achieved by utilizing and visualizing either the alignment pin 74 or alignment shim 200 with respect to a bony landmark. For example, internal-external rotational alignment may be achieved where the longitudinal axis of the alignment pin 74 or alignment end 204 of the alignment shim 200 is parallel to the posterior condylar axis or epicondylar axis of the femur when viewing the distal femur in a distal-proximal direction. FIGS. 8 and 9C are exemplary depictions of such alignment, although these figures depict an unresected distal femur. Where alignment is not achieved, a shim (not shown) may be placed between the posterior referencing guide 20 and proximal tibial resection 112 to rotate the profiling guide 30' into proper alignment. Alternatively, the operator may grip and rotate the posterior referencing guide 20 until internal-external rotational alignment is achieved.

Figure 17:
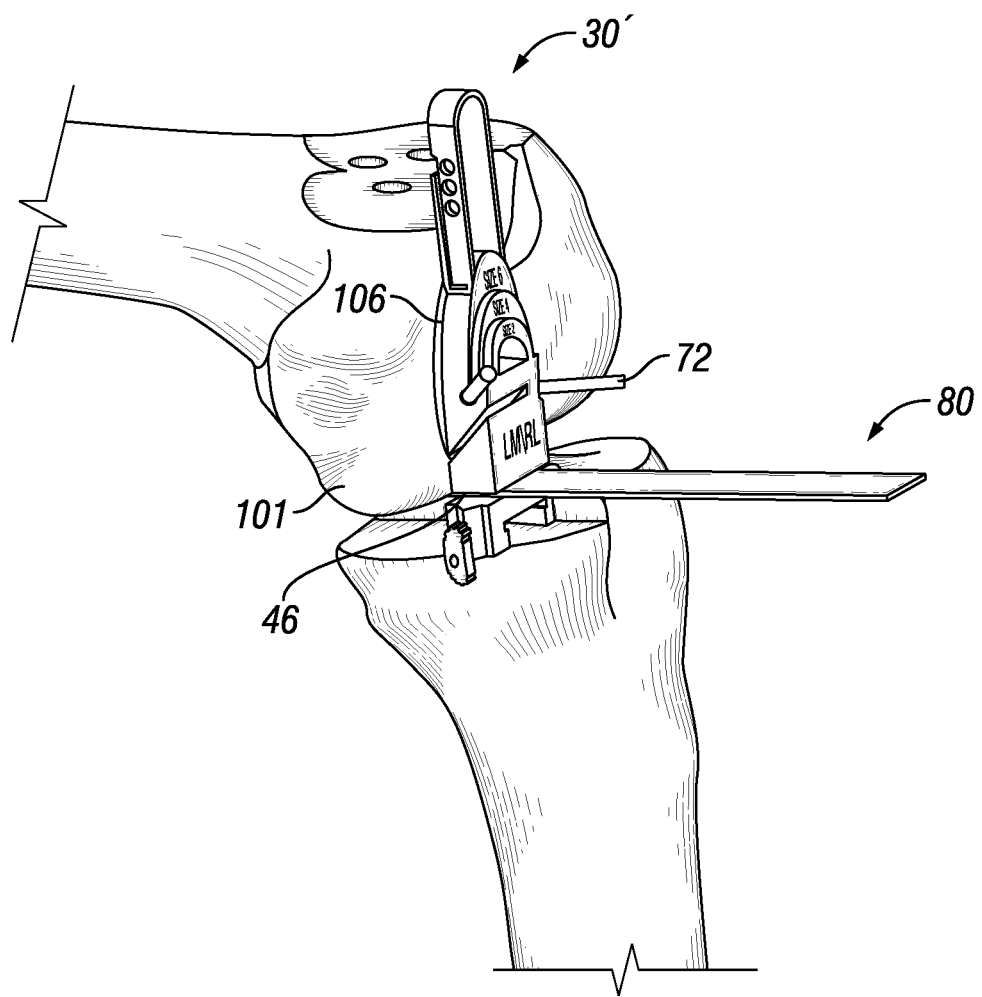
FIG. 17 is a perspective view showing the assembly of FIG. 16 with the posterior referencing guide removed and including a cutting device extending through an aperture in the profiling guide.
Figure 18:
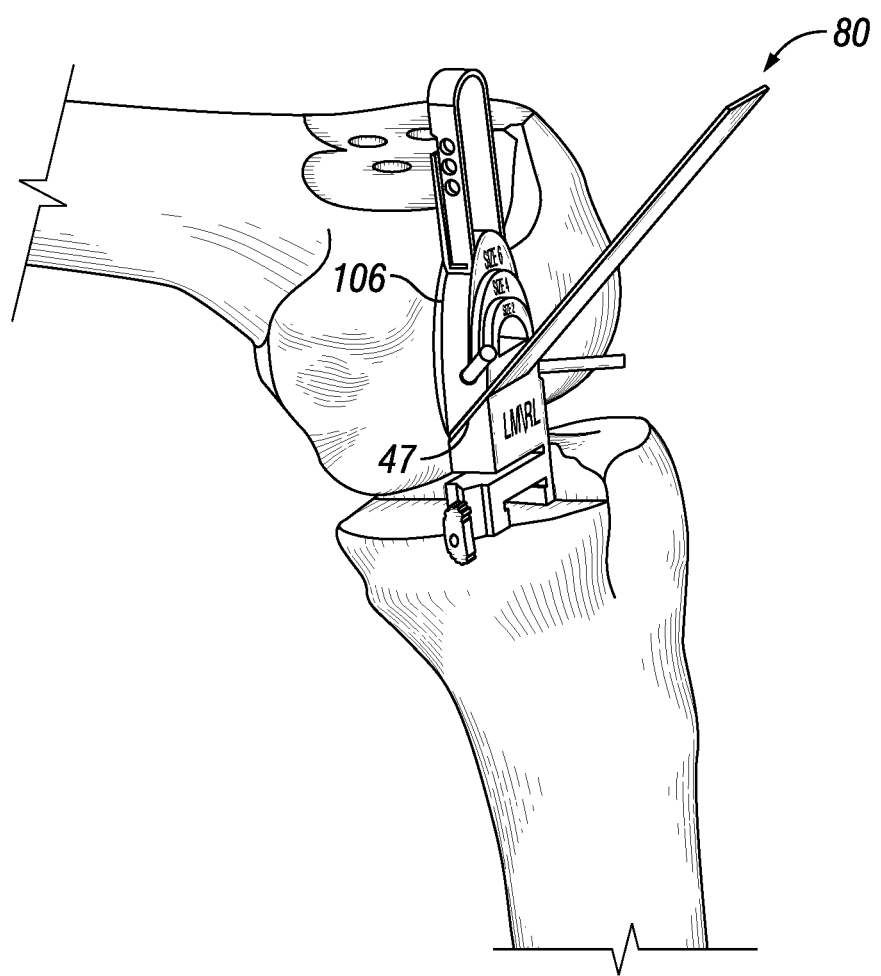
FIG. 18 is a perspective view showing the assembly of FIG. 17 including a cutting device extending through another aperture in the profiling guide.
Figure 19:
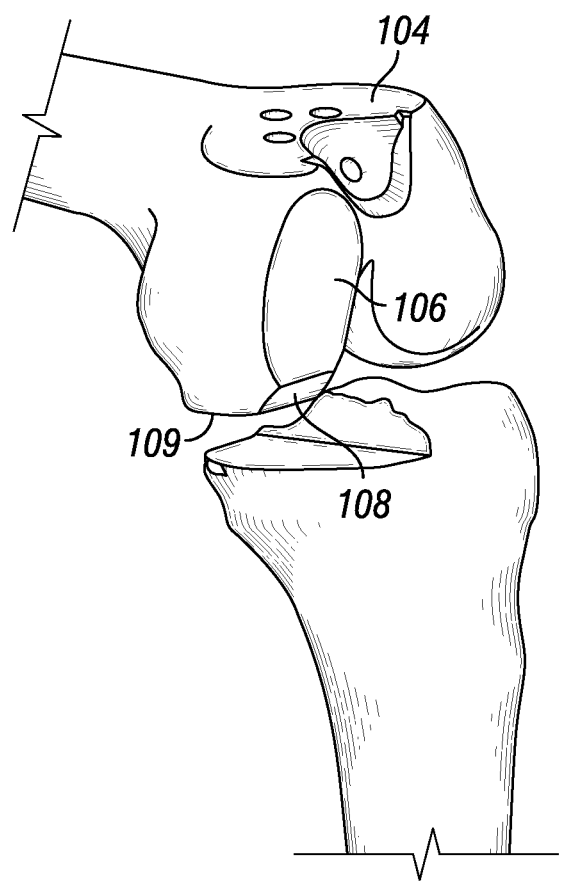
FIG. 19 is a perspective view of a femur having an anterior, distal, posterior, and chamfer resected surfaces, and a tibia having a proximal resected surface.

Thereafter the profiling guide 30' may be pinned to the femur with pin 72 in order to stabilize the profiling guide 30' during the posterior and chamfer resections. The posterior referencing guide 20 may be removed by sliding out of the first T-slot 48, or may remain in place during the resections to act as a depth stop for the posterior chamfer cut 108. A cutting device 80 may then be inserted through the first resection aperture 46 to perform a posterior resection 109 of the posterior condyle 101 as illustrated in FIG. 17 and then inserted through the second resection aperture 47 as illustrated by FIG. 18 to perform chamfer resection 108 connecting the distal and posterior resections 106, 109. However, it is noted that the chamfer resection 108 may be performed prior to the posterior resection 109. The result may be a BKA that avoids impingement between a unicondylar arthroplasty and a patellofemoral arthroplasty as shown in FIG. 19.

It is noted that the aforementioned steps can be carried out in various other sequences other than what has been described or in some situations, simultaneously. Additionally, the method can include one or more other steps not described which can be carried out before any of the defined steps, between two of the defined steps, or after all of the defined steps without departing from the inventive concept.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone resection guide, comprising:
a profiling guide having a first bone contact surface defining a first plane for contacting a first portion of a femoral condyle and a periphery defining at least a portion of an outer perimeter of the first bone contact surface, wherein the at least a portion of the outer perimeter of the first bone contact surface is dimensioned to substantially correspond to at least a portion of a periphery of a first condylar implant, the profiling guide defining a first resection aperture extending through the first bone contact surface orthogonally with respect to the first bone contact surface;
a posterior referencing guide having a second bone contact surface defining a second plane for contacting a second portion of the femoral condyle, the posterior referencing guide coupled to the profiling guide such that the first plane intersects the second plane; and
a distal resection guide defining a resection slot, the distal resection guide being adapted to couple to an extension of the profiling guide, wherein a plane extending through the resection slot is orthogonal to a plane extending through the first resection aperture when the distal resection guide is coupled to the extension.

2. The bone resection guide of claim 1, wherein the profiling guide includes a second resection aperture extending through the first bone contact surface at an oblique angle with respect to the first bone contact surface.

3. The bone resection guide of claim 2, wherein the first plane orthogonally intersects the second plane at a vertex away from the femoral condyle when the first and second bone contact surfaces contact the first and second portions of the femoral condyle, respectively.

4. A bone resection guide, comprising:
a profiling guide having a first end, a second end and a first planar bone contact surface between the first and second ends, the first planar bone contact surface defining a first plane and being bounded by a perimeter thereof that is sized and shaped to corresponds to periphery of a first implant, the profiling guide further including a projection extending from the first end thereof;
a posterior referencing guide having a second planar bone contact surface defining a second plane and being coupled to the profiling guide such that the first plane intersects the second plane; and
a distal resection guide that includes a resection slot, the distal resection guide is adapted to be coupled to the projection of the profiling guide, wherein the resection slot extends along an axis parallel to the first planar bone contact surface when the distal resection guide is coupled to the projection.

5. The bone resection guide of claim 4, wherein the posterior referencing guide is slidably attached to the second end of the profiling guide.

6. The bone resection guide of claim 4, wherein the posterior referencing guide includes a first portion and a second portion, the first portion includes the second bone contact surface, and the second portion defines a handle and defines an axis that intersects an axis of the first portion.

7. The bone resection guide of claim 4, wherein the profiling guide includes a first guide slot extending therethrough and defining a plane perpendicular to the first planar bone contact surface.

8. The bone resection guide of claim 7, wherein the profiling guide includes a second guide slot extending therethrough and defining a plane obliquely angled relative to the first guide slot.

9. The bone resection guide of claim 4, wherein the profiling guide includes a plurality of outlines each corresponding to one of a plurality of implants, wherein each of the plurality of implants is of a different size.

* * * * *